US009921105B2

(12) United States Patent
Assefa et al.

(10) Patent No.: US 9,921,105 B2
(45) Date of Patent: Mar. 20, 2018

(54) MOBILE CELLULAR SPECTROSCOPY

(71) Applicant: International Business Machines Corporation, Armonk, NY (US)

(72) Inventors: Solomon Assefa, Ossining, NY (US); Sergio A. Bermudez Rodriguez, Boston, MA (US); Levente Klein, Tuckahoe, NY (US); Theodore G. van Kessel, Millbrook, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/614,575

(22) Filed: Feb. 5, 2015

(65) Prior Publication Data

US 2016/0231171 A1 Aug. 11, 2016

(51) Int. Cl.
*G01J 3/28* (2006.01)
*G01J 3/02* (2006.01)
*G01J 3/18* (2006.01)
*G01J 3/10* (2006.01)

(52) U.S. Cl.
CPC .......... *G01J 3/2823* (2013.01); *G01J 3/0264* (2013.01); *G01J 3/0272* (2013.01); *G01J 3/0291* (2013.01); *G01J 3/18* (2013.01); *G01J 3/10* (2013.01)

(58) Field of Classification Search
CPC ........ G01J 3/28; G01J 1/00; G01J 3/00; G01J 3/2823; G01J 3/0291; G01J 3/0264; G01J 3/0272; G01J 3/18; H04M 1/00; G09G 5/00; G01C 21/30; G01B 29/12
See application file for complete search history.

(56) References Cited

U.S. PATENT DOCUMENTS 7,420,663 B2 9/2008 Wang et al.
7,889,335 B2 2/2011 Durst et al.
8,305,577 B2 11/2012 Kivioja et al.
(Continued)

FOREIGN PATENT DOCUMENTS

WO 2013191669 A2 12/2013

OTHER PUBLICATIONS

Dutta et al., "Evanescent Wave Coupled Spectroscopic Sensing Using Smartphone," IEEE Photonics Technology Letters, Mar. 15, 2014, p. 568-570, vol. 26, No. 6.
(Continued)

*Primary Examiner* — Jamil Ahmed
(74) *Attorney, Agent, or Firm* — L. Jeffrey Kelly (57) ABSTRACT

The present invention discloses a spectrometer apparatus comprising a mobile device including an integrated camera, having a camera lens and an image sensor. The camera lens is located within a body of the mobile device that comprises a detachable housing coupled to the body of the mobile device. The detachable housing includes a first end and a second end opposed to the first end. The first end includes an optical input and the second end includes an opening that is substantially aligned with the camera lens. An optical spectrometer device is located within the housing and optically coupled to both the optical input at the first end of the housing and the camera lens at the second end of the housing. The optical spectrometer device receives a target image from the optical input and generates a spectral image that is received by the image sensor via the camera lens.

19 Claims, 7 Drawing Sheets

(56) References Cited

U.S. PATENT DOCUMENTS

| | | | |
|---|---|---|---|
| 8,345,226 B2 | 1/2013 | Zhang | |
| 8,743,194 B2 | 6/2014 | Fletcher et al. | |
| 9,217,706 B2 | 12/2015 | Mucci et al. | |
| 2006/0279732 A1* | 12/2006 | Wang | G01J 3/02 356/326 |
| 2008/0086265 A1* | 4/2008 | Heuser | G09B 29/12 701/431 |
| 2011/0009163 A1* | 1/2011 | Fletcher | G02B 21/0008 455/556.1 |
| 2011/0234631 A1* | 9/2011 | Kim | G06T 15/60 345/632 |
| 2011/0261355 A1 | 10/2011 | Hannel et al. | |
| 2012/0113422 A1* | 5/2012 | Kivioja | G01J 3/0205 356/328 |
| 2016/0109371 A1 | 4/2016 | Blair | |
| 2017/0160131 A1 | 6/2017 | Goldring et al. | |

OTHER PUBLICATIONS

Gallegos et al., "Label-free biodetection using a smartphone," Lab on a Chip, 2013, pp. 2124-2132, The Royal Society of Chemistry.
Smith et al., "Cell-Phone-Based Platform for Biomedical Device Development and Education Applications," PLoS ONE, Mar. 2011, pp. 1-11, vol. 6, Issue 3.

\* cited by examiner

MOBILE CELLULAR SPECTROSCOPY

BACKGROUND

The present invention relates generally to the field of spectrometry, and more particularly to a mobile spectrometer device and analytic application.

Spectral decomposition analysis has been performed for more than 200 years in various fields of sciences with large and complex instruments. Modern iterations of spectral decomposition instruments require power and computer application control for moving optics, as sensitive control may aid in the decomposition of the original light beam into its spectral components. For certain industries, there is a need to develop small, portable, and cost effective spectrometers capable of attachment to mobile devices, for example, a cell phone or tablet, that can provide spectral images of different wavelengths at different special and temporal points. These new spectrometers may be a simple snap-on device that may be attached to a mobile device when it is necessary and may acquire images with high fidelity and resolution.

It is desired to obtain images from places where there is no other mean to obtain spectral information, e.g. a remote field/area, and validate observations that are acquired via other measurement instruments (e.g. remote measurements via a satellite). Note that remote measurements have a much coarser spatial resolution (around 1 km×1 km) when compared to the one achieved by a cell phone (1 cm×1 cm up to 1 m×1 m). In many situations, satellite images are acquired at weekly intervals, while cell phone images may be taken more frequently, resulting in more spectral information updates, for example, in crop health studies, the process may be done multiple times per day or at critical times related to certain plant development stages, depending of the needs of a particular crop.

The camera system included in many modern cell phone device have the capability to acquire spectral information in the visible and near infrared regime. The mobile device image acquisition capability is mainly limited by the optical response of the light detector (silicon in most of the cell phone devices). The wide bandwidth capability of the mobile devices allow images to be acquired in any narrow bandwidth centered on specific wavelength (by using, for example, a filter), and to extract reflection responses from the objects under study.

SUMMARY

Embodiments of the present invention discloses a spectrometer apparatus comprising a mobile device including an integrated camera, having a camera lens and an image sensor. The camera lens is located within a body of the mobile device that comprises a detachable housing coupled to the body of the mobile device. The detachable housing includes a first end and a second end opposed to the first end. The first end includes an optical input and the second end includes an opening that is substantially aligned with the camera lens. An optical spectrometer device is located within the housing and optically coupled to both the optical input at the first end of the housing and the camera lens at the second end of the housing. The optical spectrometer device receives a target image from the optical input and generates a spectral image that is received by the image sensor via the camera lens. The spectral information may be uploaded in real time to a server and can be combined with satellite acquired spectral images where the mobile device data will calibrate and validate the information acquired by satellite.

DETAILED DESCRIPTION

A system of detecting spectral information, extracting spatial and temporal variations of an spectral image or "scene," combined with a mobile device application to decompose an image in its spectral bands, process the data in real time, and extract information of interest from the images.

A transmission grating or narrow band filters may be placed in front of a mobile phone device in order to provide the image and the spectral components of the original image.

Application specific analysis may be done locally on the mobile device by an application or the data can be relayed to a host application server for further processing and recording.

In one example, an image can be a picture of a scene that is in the field of view of the camera. The reflection from a surface and/or a transmission spectrum from the object of interest are recorded. The image acquisition process is combined with real time analytics that can calculate the sun position when an image is acquired. Additional factors to consider are the expected illumination based on cloud coverage of the sky. An automatic aperture may be adjusted to acquire images under similar light conditions. If the outdoor illumination is low, the camera's light source can be used to illuminate the surface both through either reflection or transmission.

Figure 1:
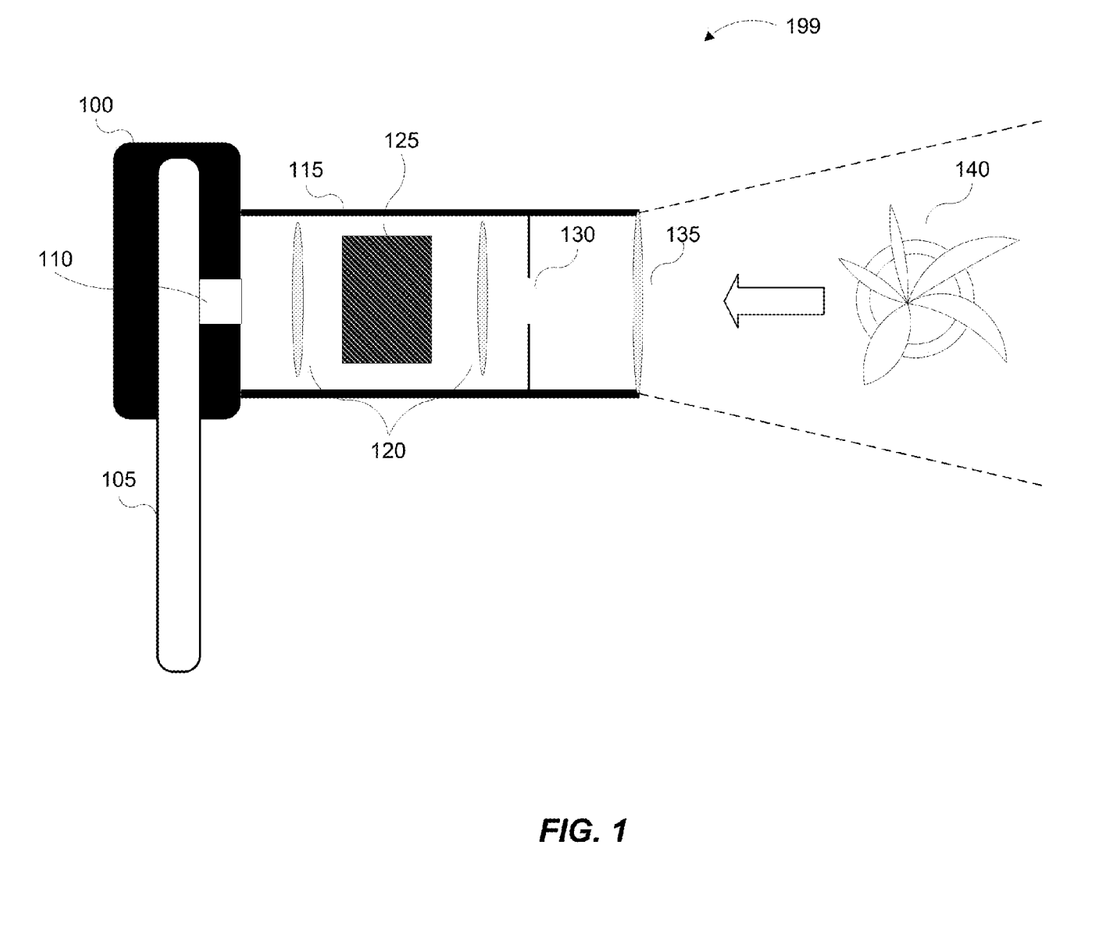
FIG. 1 is a block diagram illustrating components of the optical spectrometer apparatus, in accordance with an embodiment of the present invention.

The invention will now be discussed in referencing to the figures. FIG. 1 is a block diagram illustrating components of the optical spectrometer apparatus, in accordance with an embodiment of the present invention. A spectrometer apparatus 199 may comprise clip 100, mobile device 105, integrated camera 110, housing 115, lenses 120, grating 125, optical input 130, target lens 135, and image target 140.

In various embodiments of the invention, illumination from a light source, for example ambient light from the sun (not shown), may illuminate an image target 140. Light reflecting of image target 140 may enter target lens 135, for example a lens capable of magnification, and enter optical input 130. A series of lenses 120 may relay or collimate the light entering via optical input 130 through grating 125. Optical input 130 may be, for example, an opening in housing 115 or optically transparent cover over an opening in housing 115.

Grating 125 may be a transmission diffraction grating or reflectance grating. A reflectance grating may include a lens system, for example lenses 120, for collimating light from image target 140 onto the reflectance diffraction grating, for example grating 125, and focusing the resulting spectral image onto integrated camera 110.

The light reflected may be received by integrated camera 110 containing, for example, a complementary metal oxide semiconductor (CMOS) silicon image sensor. Integrated camera 110 may be contained within mobile device 105, attached to housing 115, via clip 100.

In an exemplary embodiment mobile device 105 may be smart phone, or other mobile communication device that may receive images through a camera and be capable of communications. In various embodiments of the invention, mobile device 105 may be connected to a laptop computer, tablet computer, netbook computer, personal computer (PC), a desktop computer, or any programmable electronic device capable of communicating with other programmable electronic devices. The communication environment of mobile device 105 is discussed below in reference to FIG. 5.

Mobile device 105 may include a computer application (not shown). The computer application may measure illumination levels received by integrated camera 110, calculate spectral indices based on measurements, record a time stamp of the generated spectral image from light passing through grating 125, and receive global positioning system (GPS) information in order to calculate solar positions at the time and location of the received spectral images.

In various embodiments of the present invention, mobile device 105 may contain a computing device for receiving, processing, and communicating spectral images via a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The computer application may analyze an image received by integrated camera 110 comprising the spectral information from the spectral image generated by grating 125. The computer application may select a wavelength of interest, for example 850 nm, that may be predetermined by a user. The received spectral information may be obtained from one or more additional generated spectral images corresponding to one or more different temporal and special points on the image target 140. For example, different spectral information may be generated by spectrometer apparatus 199 and one wavelength may be selected then spectrometer apparatus 199 may be rotated and a new spectral image may be received by integrated camera 110. The optimal wavelength may take into account the various point measurements and rotation of the camera. In various embodiments, mobile device 105 may include a gyroscope, allowing the computer application to calculate the optimal detection angle to select spectral image data.

In various embodiments grating 125 may be a visible wavelength diffraction grating. Grating 125 is positioned in the front of integrated camera 110. The image from the field of view of integrated camera 110 is focused on the camera sensor using lenses 120 for light collimation. Clip 100 may be attachable to mobile device 105 in front of integrated camera 110 where the spectral information at wavelengths covering across the detector bandwidth (visible to near IR) is acquired. Lenses 120 may relay images or focus images or both. Lenses 120 may be arranged such that the direct pass image and the spectral information may be formed at the first order interference angle are acquired.

In one embodiment, incident light enters the spectrometer clip on optical input 130 and is collimated by one of lenses 120. The collimated light is diffracted by grating 125 to one or more orders and an image received by integrated camera 110 may only utilize part or all of the active camera sensor. It is understood that the entire housing 115 may be attached and removed to allow normal use of mobile device 105 without housing 115.

Figure 2:
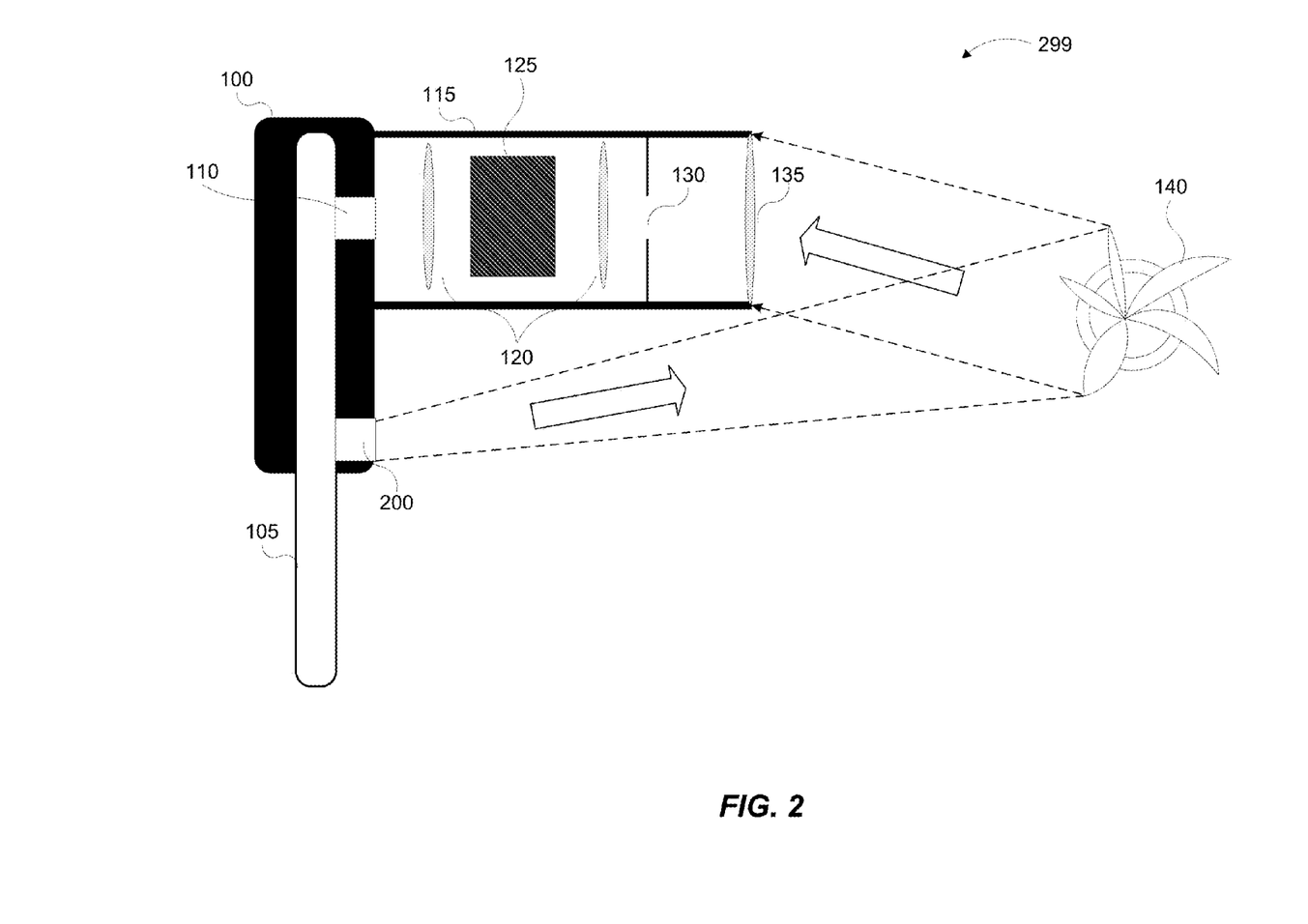
FIG. 2 is a block diagram illustrating components of the reflection spectrometer apparatus, in accordance with an embodiment of the present invention.

FIG. 2 is a block diagram illustrating components of the reflection spectrometer apparatus, in accordance with an embodiment of the present invention. The spectrometer apparatus 299 is similar to spectrometer apparatus 199. However, spectrometer apparatus 299 includes an integrated light source 200.

In various embodiments, integrated light source 200 may be mounted to a body of mobile device 105. Integrated light source 200 may allow an increase in illumination light available to illuminate image target 140. The computer application on the mobile device may control the light levels from integrated light source 200 in order to maintain consistence in illumination levels of image target 140 in varying weather conditions that may, for example cause inconsistent light, during a cloudy day, from the sun to reflect off of image target 140. Therefore, the spectral image received by integrated camera 110 may be generated from ambient light, artificial light from integrated light source 200 or a combination of these.

Figure 3:
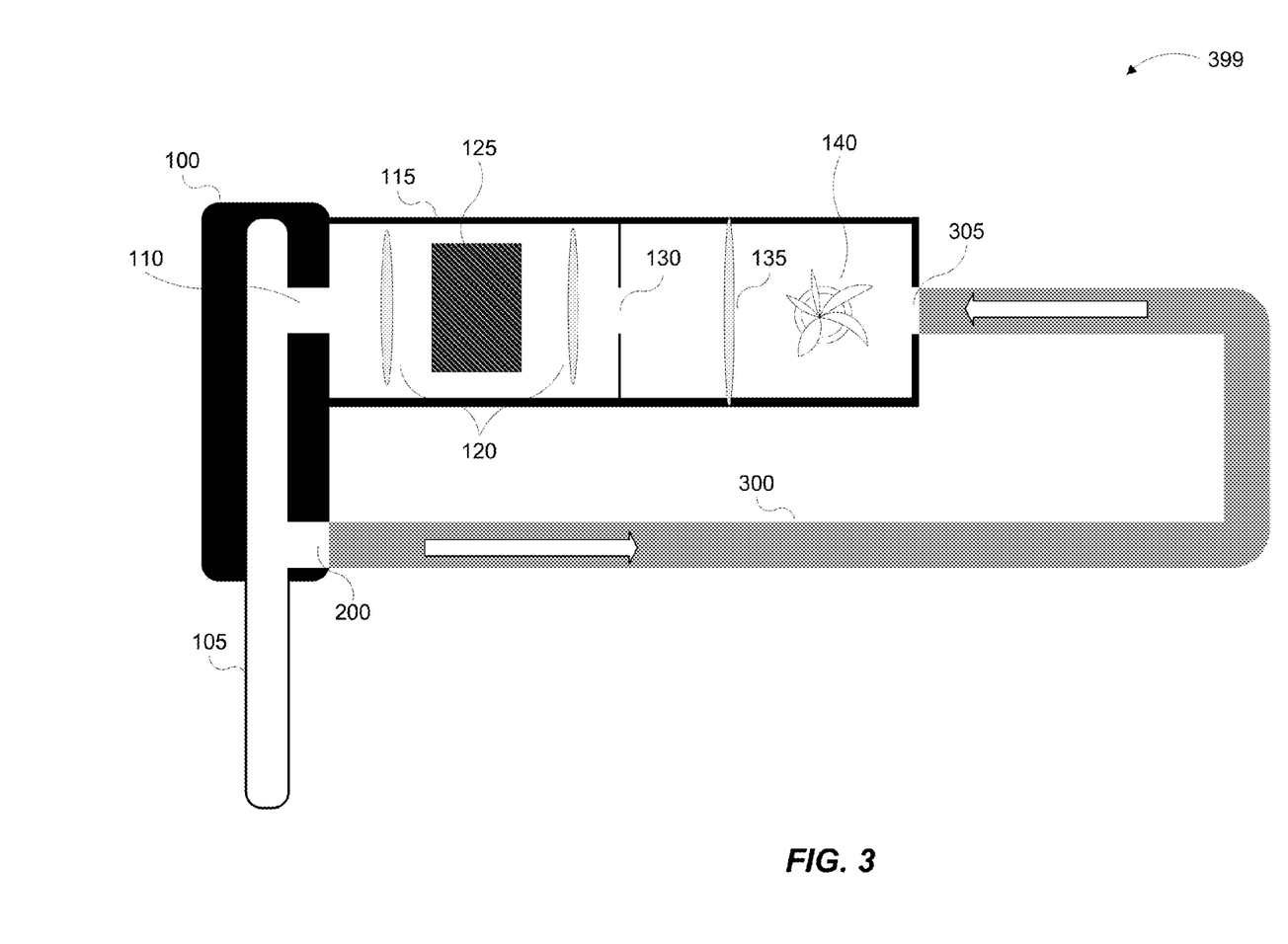
FIG. 3 is a block diagram illustrating components of the transmission spectrometer apparatus, in accordance with an embodiment of the present invention.

FIG. 3 is a block diagram illustrating components of the transmission spectrometer apparatus, in accordance with an embodiment of the present invention. The spectrometer apparatus 399 is similar to spectrometer apparatus 199 and spectrometer apparatus 299. However, spectrometer apparatus 399 includes a light guide 300 and light guide attachment 305.

Light guide 300 may be an optical waveguide that allows light from integrated light source 200 to propagated along light guide 300 and allow light to enter housing 115 at light guide attachment 305. In various embodiments, image target 140 may be located within housing 115 as shown in FIG. 3. Light entering housing 115 at light guide attachment 305 may transmit through image target 140 and propagate on through spectrometer apparatus 399.

In various embodiments, spectrometer apparatus 399 may include a cavity in housing 115 in which an image target 140 may be placed. Light guide attachment 305 may be attached at one end of this cavity to provide light into the cavity and onto image target 140. This may allow transmission spectroscopy with grating 125 a transmission grating. For example, a finger may be placed in the cavity in housing 115 that may allow the periodic transmission monitoring to pulse, blood gasses and blood chemistry in the medial field.

Figure 4:
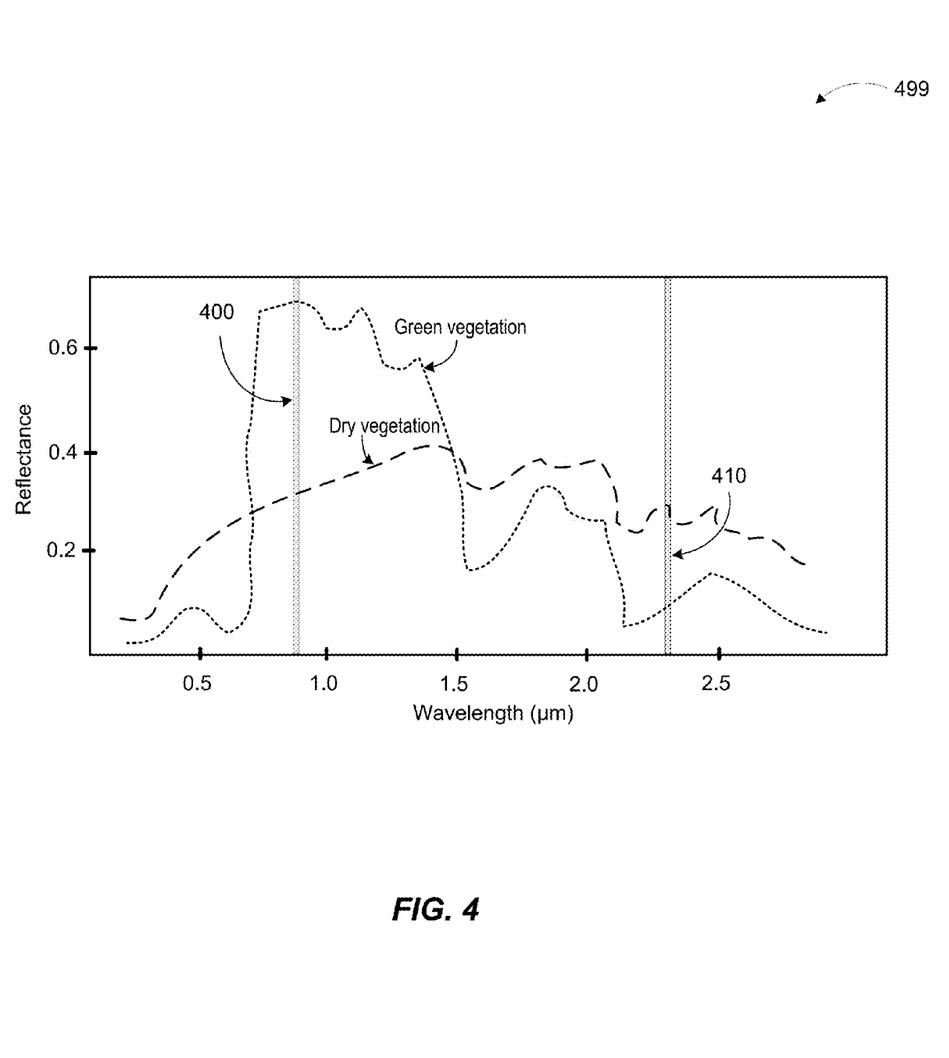
FIG. 4 illustrates the graphical representation of spectral data received from a generated spectral image.

FIG. 4 illustrates the graphical representation of spectral data received from a generated spectral image. In various embodiments of the invention, image target 140 may be a piece of vegetation or plant. For example, a farmer may want to understand the health of crops. The spectrometer apparatuses 199, 299, and/or 399 may be used to generate spectral information. The spectral information may be processed by the computer application on mobile device 105.

The computer application on mobile device 105 may allow the selection of spectral bands of interest as well as include a conversion of an acquired image value into reflected radiation values. The reflected radiation from the object of interest may be calculated based on the ambient illumination, or artificial illumination. The ambient illumination may be determined from satellite measurements, or weather data received by mobile device 105 in order to account for attenuation due to atmospheric conditions (humidity, aerosols). Such atmospheric conditions may be used to assess the amount and direction of solar radiation that is reaching the surface. FIG. 4 contains the spectral information graph 499. Spectral information graph 499 represents an example of what the computer application may generate when plotting received spectral information. The graphical format of spectral information graph 499 may be, for example, reflectance vs. wavelength. There may be a reflectance difference between green vegetation and dry vegetation. Low wavelength of interest 400 and high wavelength of interest 410 may be selected by a user or calculated by the computer application.

Analytics may be performed by the computer application on the mobile device, for example, the calculation of the normalized difference vegetation index (NDVI), soil adjusted vegetation index, soil classification index, and mapping characteristics. The normalized difference vegetation index is defined as:

$$NDVI = \frac{NIR - R}{NIR + R}$$

where NIR is near infrared and R is red reflectance of the spatial features determined from an image. For the NDVI estimation, the NIR center wavelength of interest, for example low wavelength of interest 400, may be a parameter determined by the application (typically around 850 nm) such that the difference between the reflectance from plants or crops and the soil is the maximum. This estimation of the maximum difference may be determined from a search and analysis of a set of spectral information, derived from the spectral images, received by integrated camera 110, at different wavelengths. Contrast between images may be obtained by subtracting spectral information of one image from another. Differences in the reflection from the soil, the NDVI, may be affected by the soil variation properties, for example, composition or water retention, and may cause a convoluted response output of the computer application. To overcome the influence of soil properties on the vegetation index changes another parameter of interest that may be calculated is the soil adjusted vegetation index (SAVI):

$$SAVI = \frac{NIR - R}{NIR + R + L}(1 + L)$$

where L is determined as the soil reflectance index and is determined from two points (one where the soil reflectance is light brown and the other where it is dark brown). Interpolating between the two soil types may allow a straight line to be constructed, by the computer application, that can be is subtracted from the vegetation index to obtain SAVI.

The images captured and processed by mobile device 105 may also be used to extract vegetation isolines, in order to delineate zones that may have similar reflectance allowing determinations, for example, crops that may have similar crop yield potential.

Figure 5:
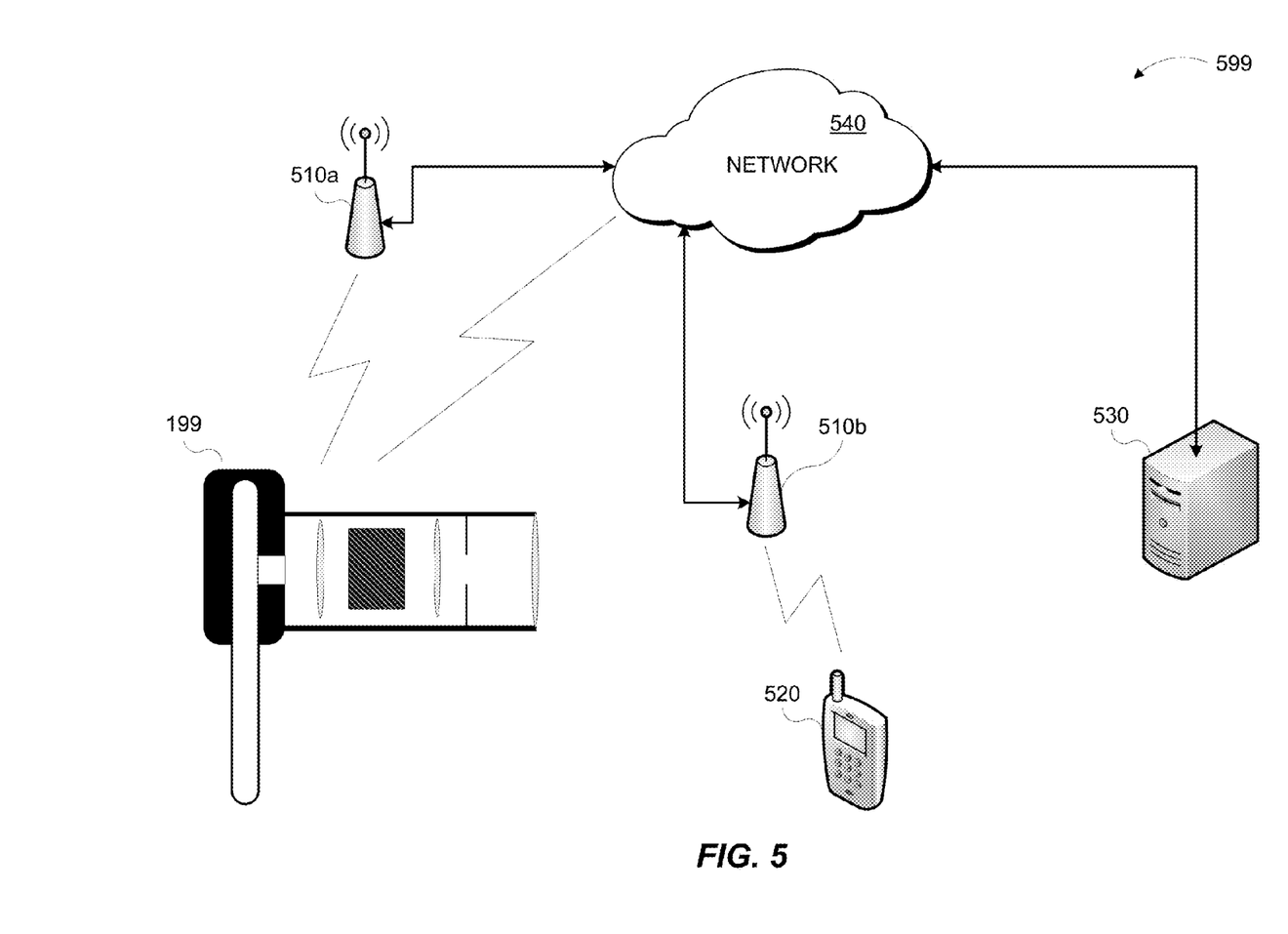
FIG. 5 is a schematic block diagram of a distributed data process environment, in accordance with an embodiment of the present invention.

FIG. 5 is a schematic block diagram of a distributed data process environment, in accordance with an embodiment of the present invention.

FIG. 5 is a schematic block diagram of a distributed data environment, in accordance with embodiment of the invention. The distributed data environment 599 includes a spectrometer apparatus 199, a wireless receiver 510*a*, a wireless receiver 510*b*, a mobile device 520 and a computer server 530, all interconnected over network 540. The computer server 530 may include instructions for analysis, weather condition data, global positioning system data, spectro-analysis software, or other forms of electronic communications which can be accessed by spectrometer apparatus 199, a wireless receiver 510*a*, a wireless receiver 510*b*, a mobile device 520 and a computer server 530 through network 540.

Network 540 can be, for example, a local area network (LAN), a wide area network (WAN) such as the Internet, or a combination of the two, and can include wired or wireless connections. In general, network 540 can be any combination of connections and protocols that will support communications via various channels between the spectrometer apparatus 199, the wireless receiver 510*a*, the wireless receiver 510*b*, the mobile device 520 and the computer server 530, in accordance with an embodiment of the invention. Network 540 may form any type of communication fabric through which data is sent and received. One example of network 540 may be intranet or the Internet.

Although the embodiments of the invention described herein are directed to a spectral decomposition application, it will be appreciated by those of skill in the art that embodiments are not limited to vegetation analysis, but instead can be practiced with all forms of spectral decomposition applications, such as, human health genetics, laboratory analysis and educational applications.

The computer server 530 may be a web server may host, instructions for analysis, weather condition data, vegetation index data, global positioning system data, spectro-analysis software, or other forms of electronic communications; enabling the spectrometer apparatus 199, and the mobile device 520 to send and receive electronic communications and data via network 540. While FIG. 5 illustrates a single computer server 530, it is noted for clarity that multiple servers may be used to implement transition of information. The computer server 530 may be a laptop computer, tablet computer, netbook computer, personal computer (PC), a desktop computer, a personal digital assistant (PDA), a smart phone, or any programmable electronic device in accordance with an embodiment of the invention.

In one embodiment of the invention, the computer server 530 includes instructions for analysis, weather condition data, vegetation index data, global positioning system data, spectro-analysis software, or other forms of electronic information. Alternative embodiments of the present invention may store such data on other devices shown in distributed data environment 599, including but not limited to the spectrometer apparatus 199, and the mobile device 520. As an example, the spectrometer apparatus 199 may access instructions for analysis, weather condition data, vegetation index data, global positioning system data, spectro-analysis software, or other forms of electronic communications by accessing storage device located on and the mobile device 520.

The computer server 530 may include instructions for analysis containing steps and alphanumeric codes associated with the steps. For example, the instructions for analysis may contain maps of the alphanumeric code wherein the codes is converted to an instruction in the computer server 530; the instruction is then transmitted back to instruction execution application for execution on the spectrometer apparatus 199, or the mobile device 520 mobile device.

The computer server 530 may generate GPS data from satellite positioning data obtained by periodically querying a satellite positioning data server for the satellite positioning data for a plurality of satellites. The computer server 530 may assign the GPS data a configurable expiration time. The computer server 530 may automatically refreshes the GPS data prior to its expiration and make it available through network 540 for download via the wireless receivers 510*a* and 510*b*.

The computer server 530 may also include a vegetation index data. The vegetation index data may contain plant measurements of a particular crop to enable the utilization of the obtained measurements and quantities of characteristic values of a specific type of plant. Such data, for example, may be utilized for determining the current nitrogen content of the plants being measured. Based on the determined nitrogen content it is then possible to draw up a suitable fertilization plan for the monitored corp.

The computer server 530 may also include spectral analysis software. Spectral analysis software may include data and mathematical algorithms for analyzing, displaying, and presenting, useful results about the objects analyzed by the spectrometer apparatus 199.

Computer server 530 may determine crop health upon receiving information from the spectrometer apparatus 199 and running the spectral analysis software. After crop health is determined, it may be transmitted via network 540 to the mobile device 520 or the spectrometer apparatus 199.

Figure 6:
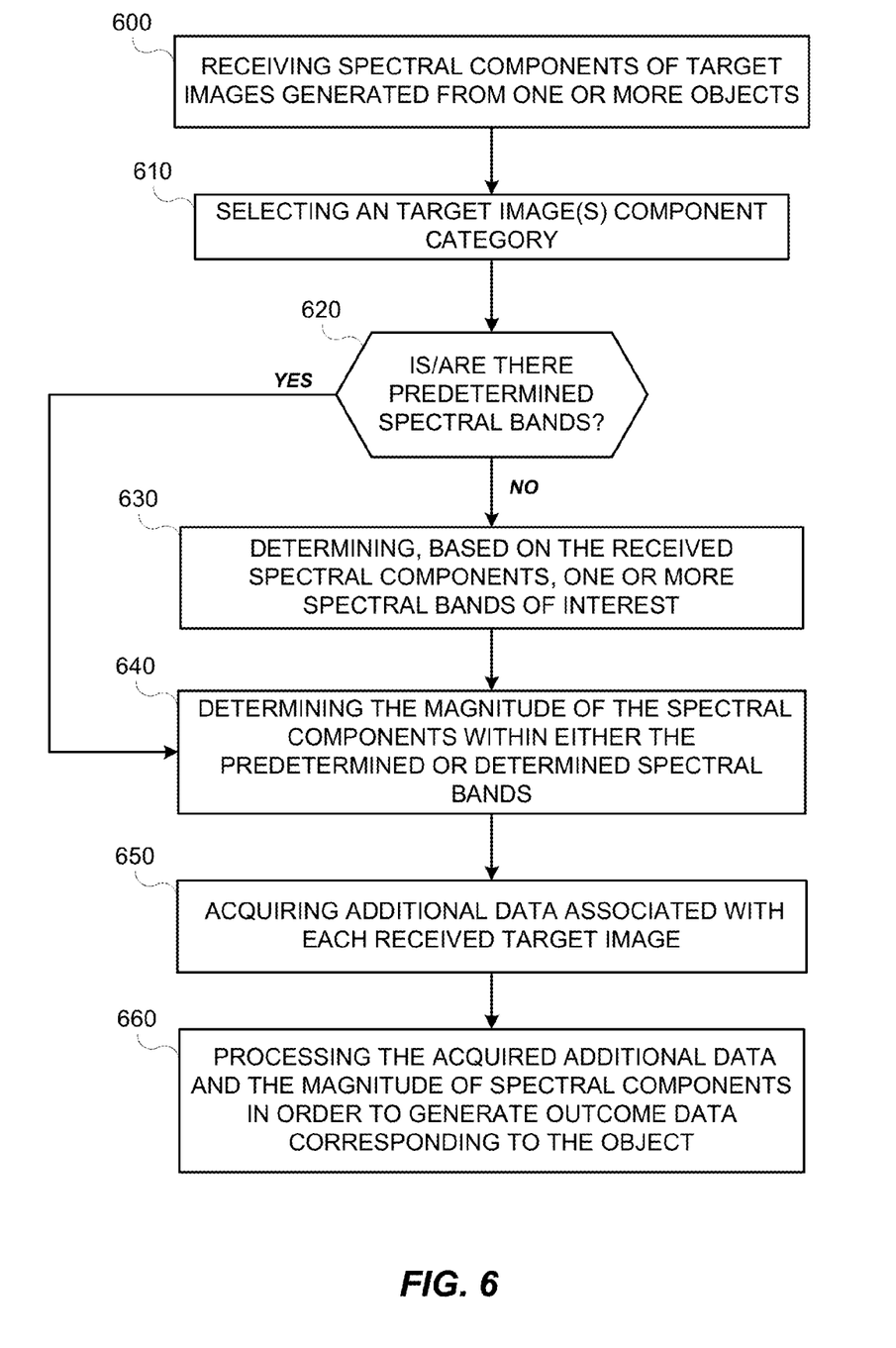
FIG. 6 is a flowchart depicting operational steps of an optical spectrometer apparatus of FIG. 1, generating a spectral image, in accordance with an embodiment of the present invention.

FIG. 6 is a flowchart depicting operational steps of an optical spectrometer apparatus of FIG. 1, generating a spectral image, in accordance with an embodiment of the present invention.

In various embodiments, a user interacts with a computer application on mobile device 105. A spectral image is received by integrated camera 110 that was generated from an image target 140. The computer application stores the spectral components of the target image 140 in memory on mobile device 105 (step 600). The user selects image components and identify various components, for example, known spectral characteristics: vegetation (green), sky (blue), soil (brown) (step 610).

If the user has not predetermined spectral bands of interest (decision step 620 "NO" branch) one or more spectral bands of interest are calculated by the computer application (step 630). The computer application determines the magnitude of the spectral components within the calculated wavelength bands (step 640). If the user identifies wavelengths of interest (decision step 620 "YES" branch) the computer application determines the magnitude of the spectral components within the predetermined bands (step 640).

Additional information associated with each received target image is acquired (step 650), for example, positioning information from a GPS or gyroscope within mobile device 105. Additional information may be provided by the user for example, in an image of a plant, soil baseline from reflectance of two different soil types can be identified, if soil has moisture or it is dry can be determined and using the calculated wavelengths from the spectral information from the images using Red wavelength and NIR, the dry soil reflectance is determined, and the soil baseline is extracted from the vegetation index.

The computer application processes the additional information and generates a spectral output (step 660) in order to communicate to the user. The user receives the information and may accept, reject, edit, or request new spectral data. For example, the received spectral information may be on a map overlay there the vegetation indexes are displayed in isolines. A user may accept or reject the communicated isolines by verifying that the vegetation isolines are not overlapping anywhere on the communicated map overlay with zones of bare soil. If there is an overlap, the user may zoom into the pictures to obtain image at higher magnification and, for example, edit the isoline by selecting the overlapping isoline and moving it with an input. A new soil baseline is subtracted from the edited vegetation index and identify the new vegetation isolines are generated. The updated isoline map overlay is communicated to the user and if accepted stored in memory or uploaded to a database as described in FIG. 5.

Figure 7:
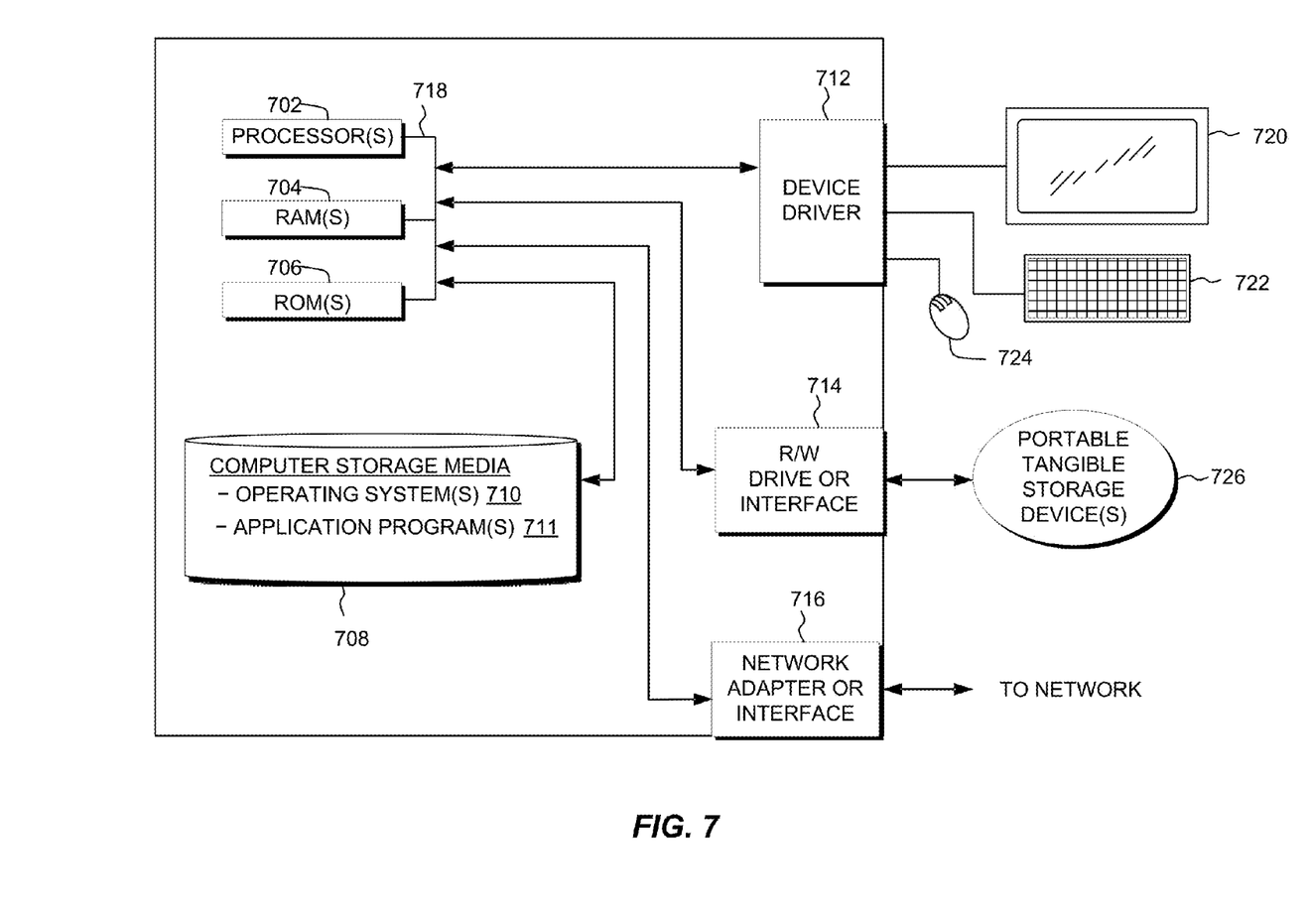
FIG. 7 depicts a block diagram of components of a mobile device within the spectrometer apparatus of FIG. 1.

FIG. 7 depicts a block diagram of components of the mobile device 105 spectrometer apparatus 199 of FIG. 1, in accordance with an embodiment of the present invention.

The components of FIG. 7 can also represent the components of spectrometer wireless receiver 510a, wireless receiver 510b, mobile device 520, and computer server 530 (FIG. 5) and is merely an example of one configuration. It should be appreciated that FIG. 7 provides only an illustration of one implementation and does not imply any limitations with regard to the environments in which different embodiments may be implemented. Many modifications to the depicted environment may be made.

Mobile device 105 may include one or more processors 702, one or more computer-readable RAMs 704, one or more computer-readable ROMs 706, one or more computer readable storage media 708, device drivers 712, read/write drive or interface 714, network adapter or interface 716, all interconnected over a communications fabric 718. Communications fabric 718 may be implemented with any architecture designed for passing data and/or control information between processors (such as microprocessors, communications and network processors, etc.), system memory, peripheral devices, and any other hardware components within a system.

One or more operating systems 710, and one or more application programs 711, for example, the computer application described above, are stored on one or more of the computer readable storage media 708 for execution by one or more of the processors 702 via one or more of the respective RAMs 704 (which typically include cache memory). In the illustrated embodiment, each of the computer readable storage media 708 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Mobile device 105 may also include a R/W drive or interface 714 to read from and write to one or more portable computer readable storage media 726. Application programs 711 on mobile device 105 may be stored on one or more of the portable computer readable storage media 726, read via the respective R/W drive or interface 714 and loaded into the respective computer readable storage media 708.

Mobile device 105 may also include a network adapter or interface 716, such as a TCP/IP adapter card or wireless communication adapter (such as a 4G wireless communication adapter using OFDMA technology). Application programs 711 on mobile device 105 may be downloaded to the computing device from an external computer or external storage device via a network (for example, the Internet, a local area network or other wide area network or wireless network) and network adapter or interface 716. From the network adapter or interface 716, the programs may be loaded onto computer readable storage media 708. The network may comprise copper wires, optical fibers, wireless transmission, routers, firewalls, switches, gateway computers and/or edge servers.

Mobile device 105 may also include a display screen 720, a keyboard or keypad 722, and a computer mouse or touchpad 724. Device drivers 712 interface to display screen 720 for imaging, to keyboard or keypad 722, to computer mouse or touchpad 724, and/or to display screen 720 for pressure sensing of alphanumeric character entry and user selections. The device drivers 712, R/W drive or interface 714 and network adapter or interface 716 may comprise hardware and software (stored on computer readable storage media 708 and/or ROM 706).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Based on the foregoing, a computer system, method, and computer program product have been disclosed. However, numerous modifications and substitutions can be made without deviating from the scope of the present invention. Therefore, the present invention has been disclosed by way of example and not limitation.

What is claimed is:

1. A spectrometer apparatus comprising:
a mobile device including an integrated camera, the integrated camera having a camera lens and an image sensor, wherein the camera lens is located within a body of the mobile device, wherein the mobile device further comprises a computer system, the computer system comprising:
one or more computer processors;
one or more non-transitory computer-readable storage media;
program instructions stored on the computer-readable storage media for execution by at least one of the one or more processors, the program instructions comprising:
instructions to receive spectral measurements of one or more illuminated target images, wherein the received spectral measurements includes at least a near infrared value, a red index value, and a soil reflectance value, and wherein the soil reflectance value is based on receiving two or more points of soil reflectance;
in response to instructions to receive a first user input selection, the user input selection being a known spectral characteristic value, instructions to calculate a first spectral index, wherein the first spectral index is based on the received spectral measurements and an illumination value;
instructions to communicate the first spectral index;
instructions to receive variable data, variable data comprising one or more of time data, location data, tabular data, topographical data, vegetation image data, and atmospheric data;
instructions to generate a second spectral index based on the first spectral index and the received variable data, wherein the generated second spectral index includes a first set of graphical isoline data, wherein the first set of graphical isoline data is based on the first spectral index and the received variable data;
instructions to communicate the second spectral index;
in response to a second user input selection instructions to modify the second spectral index based on the second user input selection;
instructions to generate a second set of graphical isoline data for display, wherein the generated second set of graphical isoline data is based on the modified second spectral index, variable data, and second user input selection;
a detachable housing coupled to the body of the mobile device, the detachable housing including a first end and a second end opposed to the first end, the first end including an optical input and the second end having an opening that is aligned with the camera lens; and
an optical spectrometer device located within the detachable housing and optically coupled to both the optical input at the first end of the detachable housing and the camera lens at the second end of the detachable housing, the optical spectrometer device receiving a target image from the optical input and generating a spectral image that is received by the image sensor via the camera lens.

2. The apparatus of claim 1, wherein the image sensor comprises a complementary metal oxide semiconductor (CMOS) silicon image sensor.

3. The apparatus of claim 1, wherein the integrated camera further comprises a computer application to measure illumination, record a time stamp of the generated spectral image, and receive global positioning system (GPS) information to calculate solar positions at the location and time of the received spectral image.

4. The apparatus of claim 1, further comprising:
receiving spectral information from the generated spectral image;
selecting a wavelength of interest; and
receiving spectral information from one or more additional generated spectral images corresponding to one or more different temporal and special points.

5. The apparatus of claim 1, wherein the optical spectrometer comprises a transmission spectrometer.

6. The apparatus of claim 5, wherein the transmission spectrometer further comprises a transmission diffraction grating comprises a lens system for collimating the target image onto the transmission diffraction grating and focusing the spectral image onto the image sensor via the camera lens.

7. The apparatus of claim 6, wherein the lens system comprises magnifying lenses.

8. The apparatus of claim 6, further comprising a slit located at the first end of the detachable housing, wherein the target image is received by the lens system thorough an opening of the slit.

9. The apparatus of claim 1, wherein the optical input comprises one of an opening and an optically transparent cover.

10. The apparatus of claim 1, wherein the optical spectrometer comprises a reflection spectrometer.

11. The apparatus of claim 10, wherein the reflection spectrometer comprises a reflectance diffraction grating.

12. The apparatus of claim 11, wherein the reflection spectrometer comprises a lens system for collimating the target image onto the reflectance diffraction grating and focusing the spectral image onto the image sensor via the camera lens.

13. The apparatus of claim 12, wherein the lens system comprises magnifying lenses.

14. The apparatus of claim 12, wherein the optical input comprises a slit located at the first end of the detachable housing, wherein the target image is received by the lens system thorough an opening of the slit.

15. A spectrometer apparatus comprising:
a mobile device including an integrated camera and light source, the integrated camera having a camera lens and an image sensor, wherein the camera lens and light source are mounted to a body of the mobile device;
a detachable housing coupled to the body of the mobile device, the detachable housing including a first end and a second end opposed to the first end, the first end including an optical input and the second end having an opening that is aligned with the camera lens;

an optical spectrometer device located within the detachable housing and optically coupled to both the optical input at the first end of the detachable housing and the camera lens at the second end of the detachable housing, the optical spectrometer device receiving, from the optical input, a target image illuminated by the light source, wherein the optical spectrometer generates, from the received illuminated target image, a spectral image that is received by the image sensor via the camera lens;

wherein the mobile device further comprises a computer system, the computer system comprising:

one or more computer processors;

one or more non-transitory computer-readable storage media;

program instructions stored on the computer-readable storage media for execution by at least one of the one or more processors, the program instructions comprising:

instructions to receive spectral measurements of one or more illuminated target images, wherein the received spectral measurements includes at least a near infrared value, a red index value, and a soil reflectance value, and wherein the soil reflectance value is based on receiving two or more points of soil reflectance;

in response to instructions to receive a first user input selection, the user input selection being a known spectral characteristic value, instructions to calculate a first spectral index, wherein the first spectral index is based on the received spectral measurements and an illumination value;

instructions to communicate the first spectral index;

instructions to receive variable data, variable data comprising one or more of time data, location data, tabular data, topographical data, vegetation image data, and atmospheric data;

instructions to generate a second spectral index based on the first spectral index and the received variable data, wherein the generated second spectral index includes a first set of graphical isoline data, wherein the first set of graphical isoline data is based on the first spectral index and the received variable data;

instructions to communicate the second spectral index;

in response to a second user input selection instructions to modify the second spectral index based on the second user input selection;

instructions to generate a second set of graphical isoline data for display, wherein the generated second set of graphical isoline data is based on the modified second spectral index and second user input selection; and in response to a second user input selection instructions to modify the second spectral index based on the second user input selection.

16. The apparatus of claim 15, wherein the optical spectrometer device comprises:

a transmission spectrometer; and a lens system for collimating the illuminated target image onto a transmission diffraction grating and focusing the spectral image onto the image sensor via the camera lens.

17. The apparatus of claim 15, wherein the optical spectrometer device comprises:

a reflection spectrometer;

a lens system for collimating the illuminated target image onto a reflectance diffraction grating and focusing the spectral image onto the image sensor via the camera lens; and the optical input comprising a slit located at the first end of the detachable housing, wherein the target image is received by the lens system thorough an opening of the slit.

18. A spectrometer apparatus comprising:

a mobile device including an integrated camera and light source, the integrated camera having a camera lens and an image sensor, wherein the camera lens and light source are mounted to a body of the mobile device;

wherein the mobile device further comprises a computer system, the computer system comprising:

one or more computer processors;

one or more non-transitory computer-readable storage media;

program instructions stored on the computer-readable storage media for execution by at least one of the one or more processors, the program instructions comprising:

instructions to receive spectral measurements of one or more illuminated target images, wherein the received spectral measurements includes at least a near infrared value, a red index value, and a soil reflectance value, and wherein the soil reflectance value is based on receiving two or more points of soil reflectance;

in response to instructions to receive a first user input selection, the user input selection being a known spectral characteristic value, instructions to calculate a first spectral index, wherein the first spectral index is based on the received spectral measurements and an illumination value;

instructions to communicate the first spectral index;

instructions to receive variable data, variable data comprising one or more of time data, location data, tabular data, topographical data, vegetation image data, and atmospheric data;

instructions to generate a second spectral index based on the first spectral index and the received variable data, wherein the generated second spectral index includes a first set of graphical isoline data, wherein the first set of graphical isoline data is based on the first spectral index and the received variable data;

instructions to communicate the second spectral index;

in response to a second user input selection, instructions to modify the second spectral index based on the second user input selection;

instructions to generate a second set of graphical isoline data for display, wherein the generated second set of graphical isoline data is based on the modified second spectral index and second user input selection;

a detachable housing coupled to the body of the mobile device, the detachable housing including a first end and a second end opposed to the first end, the first end including an optical input and the second end having an opening that is aligned with the camera lens;

an optical waveguide having a first end and a second end opposed to the first end, the first end of the optical waveguide optically coupled to the light source and the second end of the optical waveguide optically coupled to the optical input of the detachable housing; and an optical spectrometer device located within the detachable housing and optically coupled to both the optical input at the first end of the detachable housing, further comprising a slit located at the first end of the detachable housing, wherein the target image is received by the lens system thorough an opening of the slit, and the camera lens at the second end of the detachable housing, the optical spectrometer device receiving, from the optical input, a target image illuminated by the light source via the optical waveguide, wherein the optical spectrometer generates, from the received illuminated target image, a spectral image that is received by the image sensor via the camera lens.

19. The apparatus of claim 18, wherein the detachable housing comprises a cavity region that is coupled to the second end of the optical waveguide and coupled to the optical input of the detachable housing, the cavity receiving a sample that is illuminated by the light source via the optical waveguide to generate the illuminated target image, and wherein the illuminated target image is received by the optical spectrometer device via the optical input.

* * * * *